(12) United States Patent
Palma et al.

(10) Patent No.: US 8,229,569 B1
(45) Date of Patent: Jul. 24, 2012

(54) SILICONE MOLDED CO-POLYMER COMPOSITE LEAD BODY FOR PACING AND DEFIBRILLATION LEADS

(75) Inventors: Christine Palma, San Jose, CA (US); Vivek Sharma, Los Angeles, CA (US); Peter Fong, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 248 days.

(21) Appl. No.: 12/705,262

(22) Filed: Feb. 12, 2010

Related U.S. Application Data

(62) Division of application No. 11/932,676, filed on Oct. 31, 2007, now abandoned.

(51) Int. Cl.
*A61N 1/05* (2006.01)
(52) U.S. Cl. .................. 607/115; 607/116; 607/119
(58) Field of Classification Search ............ 607/112, 607/115–119
See application file for complete search history.

(56) References Cited

U.S. PATENT DOCUMENTS

| | | | |
|---|---|---|---|
| 4,019,633 A * | 4/1977 | Roth | 206/364 |
| 6,534,618 B1 | 3/2003 | Jacobs et al. | |
| 6,673,025 B1 * | 1/2004 | Richardson et al. | 600/585 |
| 6,968,237 B2 * | 11/2005 | Doan et al. | 607/122 |
| 7,060,750 B2 | 6/2006 | Jansen et al. | |
| 2006/0259033 A1 * | 11/2006 | Nesbitt | 606/45 |

OTHER PUBLICATIONS

NonFinal Office Action, mailed Apr. 15, 2009: Parent U.S. Appl. No. 11/932,676.
Final Office Action, mailed Nov. 27, 2009: Parent U.S. Appl. No. 11/932,676.

\* cited by examiner

*Primary Examiner* — Carl H Layno
*Assistant Examiner* — Pamela M Bays

(57) ABSTRACT

A composite lead body includes a rigid polymer material, such as silicone-polyurethane co-polymers, in a proximal portion of the lead body and a flexible polymer material, such as silicone, in a distal portion of the lead body. The flexible polymer material is molded in-situ about the end of the rigid polymer material, which is pre-formed, forming a junction at which the two polymers are bonded together, preferably in an interdigitated manner. The end of the rigid polymer is treated with a primer in order to facilitate the formation of a strong bond between the polymers. The molding process, advantageously, provides substantial control over the final shape of the molded polymer, inhibiting the formation of discontinuities in the shape of the lead body.

20 Claims, 7 Drawing Sheets

SILICONE MOLDED CO-POLYMER COMPOSITE LEAD BODY FOR PACING AND DEFIBRILLATION LEADS

CROSS REFERENCE TO RELATED APPLICATIONS

This application is a division of copending U.S. patent application Ser. No. 11/932,676, filed Oct. 31, 2007.

FIELD OF THE INVENTION

The invention relates generally to implantable medical devices, such as pacemakers and implantable cardioverter defibrillators (ICDs) and, in particular, concerns composite leads for implantable medical devices which possess a substantially rigid co-polymer proximal portion joined to a substantially flexible polymer distal portion, providing a strong, substantially smooth and flexible transition between distal and proximal portions.

BACKGROUND OF THE INVENTION

Implantable medical devices such as pacemakers and implantable cardioverter defibrillators (ICDs) are important, life-saving technologies. When the body's own heart pacing mechanisms fail or degrade over time, life-threatening conditions such as arrhythmias and congestive heart failure may arise. Implantable medical devices monitor the electrical activity of the heart that occur with the heart contractions which pump blood. These devices further provide appropriate electrical stimulation when the heart's own pacing mechanisms function improperly or when the heart exhibits some form of arrhythmia such as cardioversion or defibrillation.

In general, implantable medical devices comprise a pulse or waveform generator, which generates a stimulating pulse or waveform, a plurality of electrodes positioned proximate the body tissue which transmit the stimulation pulses or waveforms to the body tissue, and an insulated electrical conductor which interconnects the pulse or waveform generator and the electrode. The electrode and electrical conductor are referred to as a lead. Generally, at least one electrode is positioned at a distal portion of the lead. Leads may be placed in a variety of locations on a patient's heart, depending on their individual heart condition, and allow the implantable medical devices to sense the heart's electrical activity and provide appropriate stimulation when necessary.

A common method of positioning heart stimulation leads in contact with the patient's heart is through transvenous insertion. In this process, an incision is made in a vein near the location of the implanted stimulation device casing and the heart stimulation lead is advanced through the large veins that lead to the heart. An x-ray tube, or fluoroscope, is often used to visualize the leads and heart structures so that the leads can be placed in a satisfactory position.

The composition of the lead body is subject to stringent performance requirements for both implantation and long-term service. In one aspect, it is desirable that the lead body be chemically biocompatible with body media it is exposed to in service, so as not to cause harm to the body. In another aspect, it is desirable that the lead body exhibit selected mechanical properties. For example, the distal portion of the lead should possess sufficient flexibility so as to navigate the tortuous pathways of the veins leading to the heart. Concurrently, the proximal portion of the lead should possess sufficient stiffness so as to facilitate pushing the lead through the vein, as well as sufficient wear resistance to withstand long term use within the heart, without significant erosion or scratching damage. If pronounced, these forms of damage may result in mechanical failure of the lead body.

One approach which has been developed to meet these varying performance requirements has been through the use of composite leads. Composites are material systems which combine two or more distinct materials or phases, each with its own distinctive, desirable properties, to create a new material with desirable properties that may not be present, or to the same extent, in the components alone. For example, composite lead bodies having a distal portion formed from silicone, for flexibility, and a proximal portion, formed from silicone-polyurethane co-polymers for stiffness and wear resistance, have been demonstrated.

While these composite leads possess the chemical and mechanical properties necessary for long term use within their respective portions, the junction at which the materials are joined is problematic. In some composite lead systems, medical adhesives or transition joints are employed to attach the proximal and distal portion materials together. Traditional medical adhesives can progressively weaken over time, however, reducing the bond strength between the materials and raise the risk of lead body separation and exposure of the electrical conductor to the body media. Furthermore, mechanical couplings, such as transition joints, may locally increase the stiffness and/or cross-sectional diameter of the lead about the junction to a degree where it is difficult or impossible to properly navigate the leads through the veins.

These deficiencies in the design of conventional heart stimulation leads illustrate the need for improved heart stimulation leads which impart desired chemical and mechanical characteristics to the lead body, while maintaining the ease of implantation.

SUMMARY OF THE INVENTION

In one aspect, the embodiments of the present invention provide a composite lead. The lead includes a lead body having a proximal portion formed from a first polymer material and a distal portion formed from a second polymer material. At least a portion of the first and second polymer materials is interdigitated polymers at a junction between the polymers.

In another aspect, the embodiments of the present invention provide a composite heart stimulation lead. The lead includes at least one electrical conductor substantially contained within a lead body, a substantially rigid proximal lead body portion, a substantially flexible distal lead body portion, and an electrode in electrical communication with the at least one electrical conductor. Additionally, the proximal and distal lead body portions are bonded at a junction whose diameter is substantially the same as the diameter of the proximal and distal portions.

In a further aspect, the embodiments of the present invention provide a method of forming a heart stimulation lead body. The method comprises providing a pre-formed polymer tube comprising a substantially rigid first polymer, applying a primer to at least one end of the pre-formed tube; and molding a second polymer into a tube in-situ at about the primed ends of the pre-formed polymer tube so as to join the pre-formed and molded tubes at junctions. At least a portion of the polymers are interdigitated at the junctions so as to provide a strong mechanical bond.

BRIEF DESCRIPTION OF THE DRAWINGS

These and other objects and advantages of the present invention will become more fully apparent from the following description taken in conjunction with the accompanying drawings.

DETAILED DESCRIPTION OF THE PREFERRED EMBODIMENT

Figure 1A:
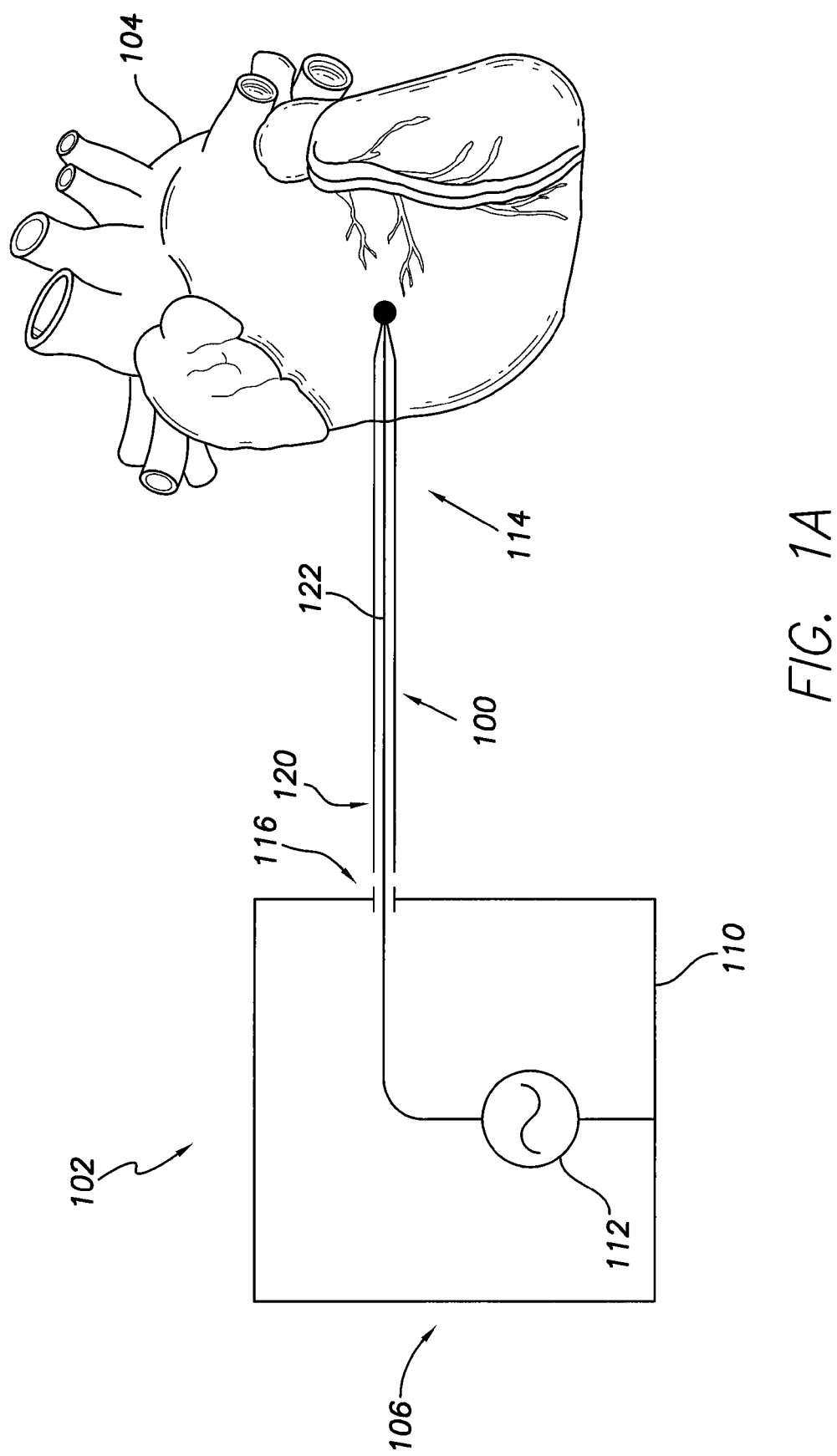
FIGS. 1A-B are schematic illustrations of one embodiment of composite heart stimulation leads of the present invention; (A) the composite heart stimulation leads employed with one embodiment of an implanted cardiac stimulation device, such as a pacemaker or ICD; (B) an enlarged view of the composite heart stimulation leads of (A), illustrating the proximal and distal portions of the lead and the junctions at which the two portions are joined.

Reference will now be made to the drawings, wherein like numerals refer to like parts throughout. Referring initially to FIG. 1A, embodiments of the invention provide a plurality of composite heart stimulation leads 100 for use with an implantable cardiac stimulation device 102 which operates in a manner known in the art so as to provide therapeutic electrical stimulation to the heart 104 of a patient. These leads can be adapted for both low voltage pacing purposes as well as higher voltage applications such as delivering cardioversion or defibrillation waveforms. Embodiments of the leads 100 employ bonding techniques which allow conventionally incompatible polymer materials, such as silicone polymers and silicone-polyurethane co-polymers, to be securely joined. Further embodiments employ polymer molding techniques which provide composite leads 100 possessing substantially smooth transitions between the joined polymers. In this manner, the composite leads 100 possess flexibility, stiffness, and wear resistance at selected locations, while substantially preserving ease of deployment and durability.

These and other advantages will be discussed in greater detail below. It may be understood that, while embodiments of the invention are discussed in reference to silicone polymers and silicone-polyurethane co-polymers, alternative embodiments may employ other polymer systems without departing from the spirit of the invention.

FIG. 1A illustrates one embodiment of an implantable cardiac stimulation device 102 in electrical communication with a patient's heart 104 by way of a plurality of composite heart stimulation leads 100. The stimulation device 102 includes a control unit 106 that has a housing 110 which encases control circuitry 112. The control circuitry 112, which preferably includes a microcontroller, determines when to deliver therapeutic electrical stimulation and also produces therapeutic electrical stimulation in a known manner. As is understood, the therapeutic electrical stimulation can comprise either low voltage pacing pulses or higher voltage cardioversion or defibrillation waveforms that are applied to the heart of the patient. Typically, the implantable cardiac stimulation device 102 also incorporates a plurality of sensors so that the control circuitry 112 receives input signals to determine when and how to apply the therapeutic electrical stimulation. Moreover, the control unit 106 also includes a battery and various other circuit components necessary to develop the therapeutic electrical stimulation pulses or waveforms. Typically, the housing 110 containing the control unit 106 is implanted adjacent the skin of the patient, for example over the pectoral muscle of the patient.

Figure 1B:
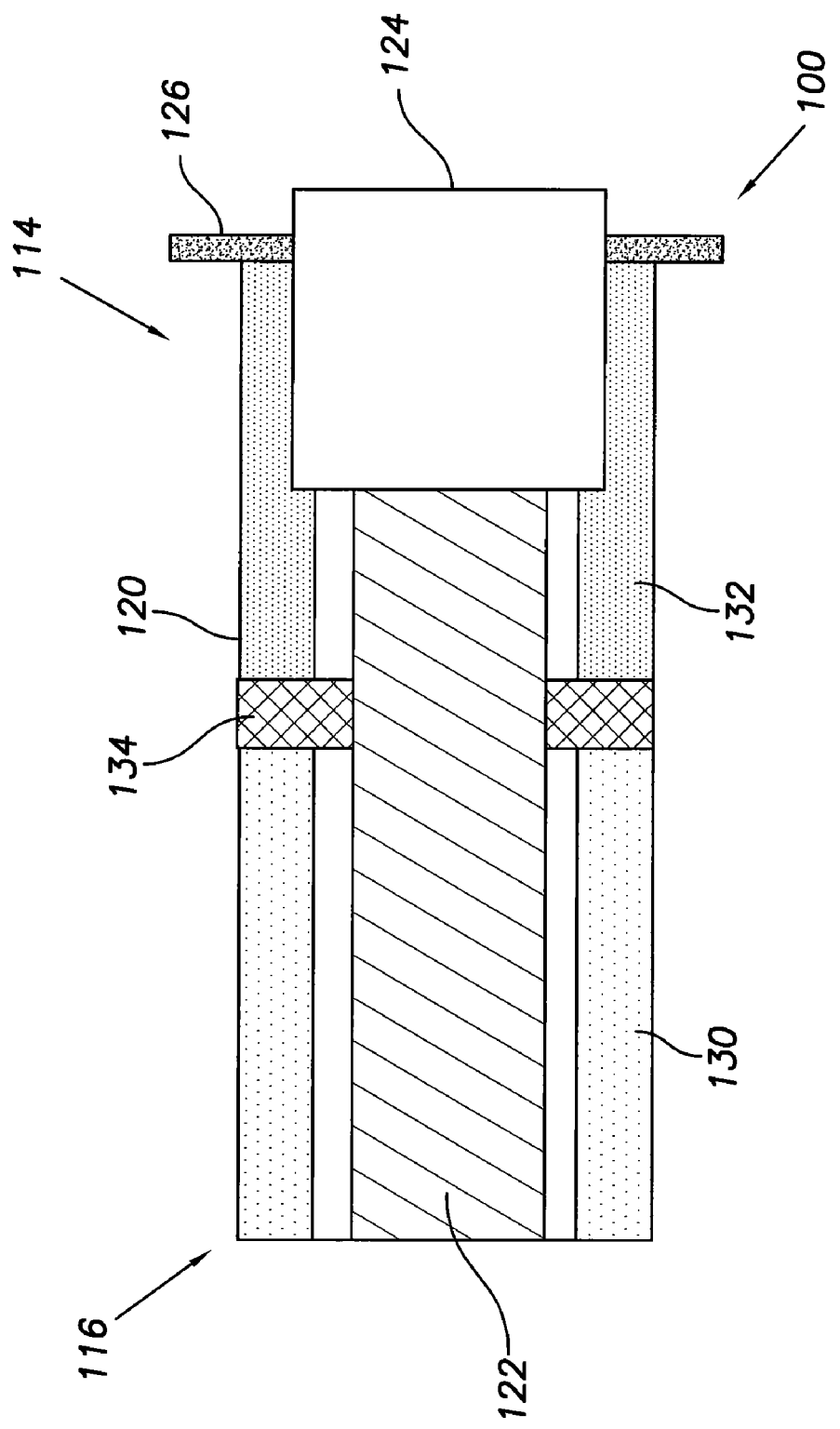

FIG. 1B illustrates an exemplary composite heart stimulation lead 100 which provides therapeutic electrical stimulation to the heart 104. The composite lead 100 possesses proximal and a distal portions 116 and 114 and an insulating lead body 120, which extends from about the housing 110 of the control unit 106 into the heart 104 of the patient. In one embodiment, the lead body 120 contains one or more electrical conductors 122 in communication with a plurality of electrodes 124 so as to be able to conduct the therapeutic electrical impulses from the control unit 106 to the heart 104. The lead body 120, electrical conductors 122, and electrodes 124 are herein referred to collectively as the lead 100.

In one embodiment, the electrodes 124 are located within about the distal portion 114 of the leads 100, however, it may be appreciated that electrodes 124 may be placed along any portion of the lead body 120, as necessary. The distal portion 114 of the leads 100 may also optionally possess a fixation mechanism 126 which can be configured to provide passive fixation or active fixation of the distal portion 114 of leads 100 to the heart 104, as generally known in the art. In one embodiment, the distal portion 114 of leads 100 may include a fixation mechanism 126 comprising tines 126 extending from the distal portion 114 of the leads 100 at an angle so as to engage the myocardium. The pressure of the leads 100 against the myocardium results in formation of a thin capsule of fibrous tissue which engages and secures the distal portion 114 of leads 100 to the myocardium in a known manner.

In general, as illustrated in the embodiment of FIG. 1B, the composite leads 100 are formed from different polymer materials which are joined together at junctions 134, where at least one of chemical and mechanical bonding occur between the polymers. The proximal portion 116 of the leads 100, in one embodiment, is formed from a polymer material which possesses relatively high strength, stiffness, and toughness, for example, silicone-polyurethane co-polymers 130 as known in the art. Advantageously, when used in the proximal portion 116 of the leads, these co-polymers 130 exhibit resistance to scratching, tearing, and wear, enhancing the durability of composite leads 100 into which they are incorporated. The stiffness of the co-polymers 130 further enhances the ease of use of the composite leads 100, as they are easier to guide through the veins leading to the heart 104 than less stiff materials. In one embodiment, the co-polymer 130 comprises OPTIM™, having the following physical properties: hardness 90 A, tensile strength 25.7 MPa, % elongation 364, tear strength 81.4 kN/m, silicone content 48% and dielectric strength 66.1.

The distal portion 114 of the leads 100, in one embodiment, comprises a plurality of highly flexible polymers, such as medical grade silicones. The flexible nature of these the silicones allows the distal portion 114 of the leads 100 to navigate the tortuous passageway through the veins to the heart 104. In one embodiment, the distal portion 114 of the leads 100 comprises an in-situ molded polymer 132. The implementation and benefits of these embodiments of the composite leads 100 are discussed in greater detail below.

Figure 2:
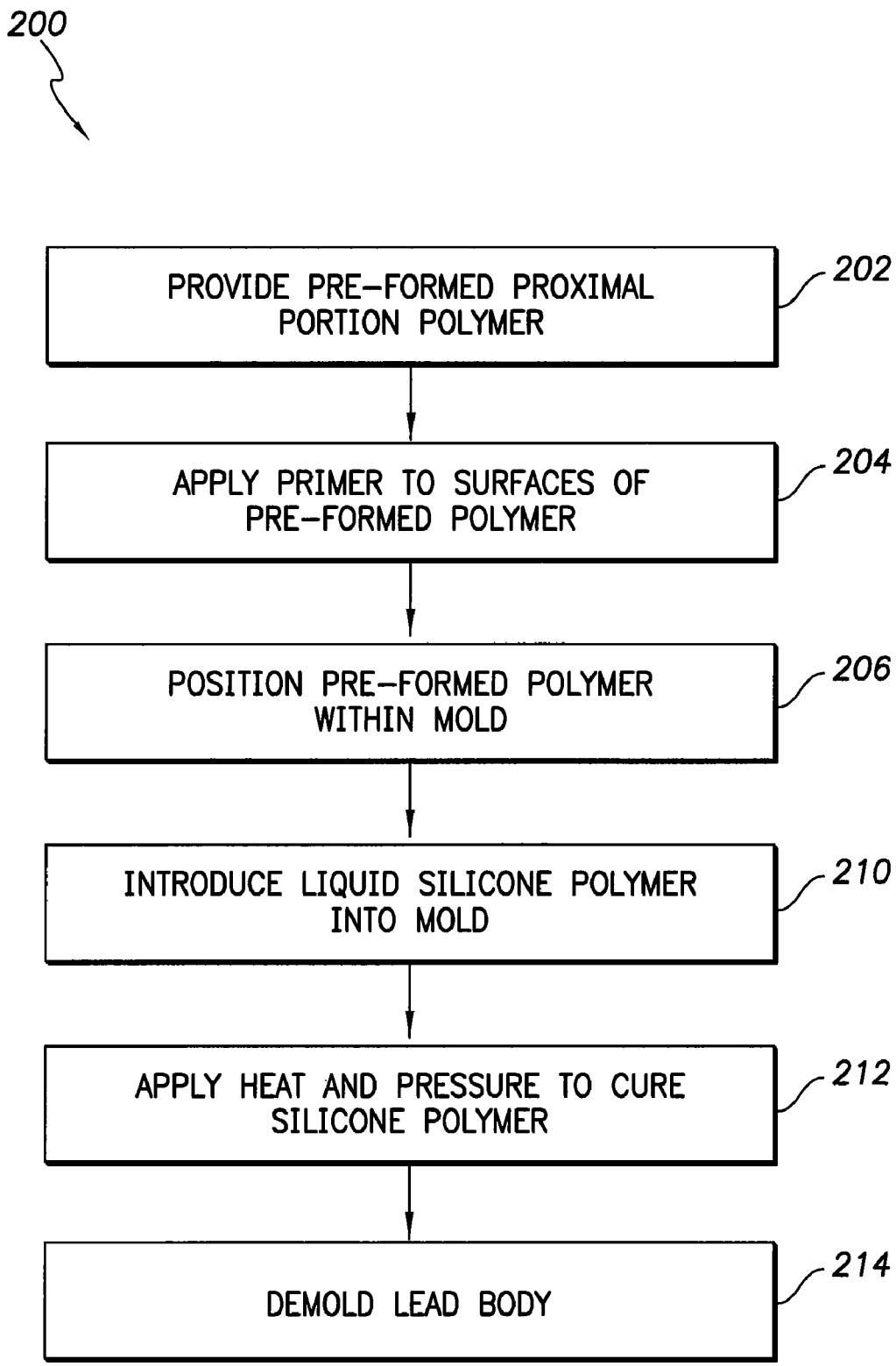
FIG. 2 is a flowchart illustrating one embodiment of a method of forming the composite leads of FIGS. 1A-B.

FIG. 2 presents a flowchart outlining a method 200 of molding the in-situ molded silicone polymer 132 to the pre-formed proximal portion polymer 130. In general, a primer is applied to surfaces of the pre-formed polymer 130 at about a location where the molded silicone polymer 132 is to be joined to the pre-formed polymer 130, such as the ends, as discussed in greater detail below with reference to FIG. 3. The molded silicone polymer 132, in a liquid form, is subsequently introduced into a mold which also receives the preformed polymer 130. The molded silicone polymer 132 thus joins the pre-formed polymer 130 at least one junction 134 (See FIG. 1B).

It may be understood that the molding procedure described below is one of many understood by those of skill in the art and that other molding techniques may be utilized without departing from the spirit of the invention. This molding process, advantageously, provides substantially greater control over the extent of the molded silicone polymer 132 within the junctions 134 between the polymers 130, 132, reducing or eliminating discontinuities in the surfaces of the junctions 134 which can inhibit passage of the composite leads 100 through the veins, while substantially maintaining the flexibility of the junction.

In further advantage, the primer 306 promotes adhesion of the joined materials, forming a strong mechanical bond between the pre-formed polymer 130 and the molded polymer 132. Adhesion may comprise at least one of chemical and physical bonding and is enhanced in at least two ways by the primer 306. In one aspect, primer allows the surfaces of the pre-formed polymer 130 to be more easily wet by the liquid silicone polymer 132, allowing the liquid silicone 132 to achieve coverage over a greater area than in comparable unprimed surfaces. This increased coverage area provides more sites for bonding of OH or C=O groups on the surfaces of the polymers 130, 132 through van der Walls forces or weak hydrogen attraction.

In another aspect, the wetting behavior promoted by the primers 306 also promotes interdigitation of the liquid silicone 132 and the pre-formed polymer 130. Interdigitation is a process where two or more materials penetrate within each other, often through tortuous pathways. When separating the materials, the interpenetrating portions of the materials frictionally side past one another, resisting the separation. This resistance is generally increased with the area of frictional contact between the materials.

Provided a wettable, pre-formed polymer surface, the liquid silicone 132 may substantially spread along irregularities found on the surfaces of the pre-formed polymer 130, such as peaks and valleys. By substantially following the contours of the valleys, the liquid silicone 132 penetrates within the surface of the preformed polymer 130. Concurrently, by substantially following the contours of the peaks, the liquid silicone 132 allows 130 penetration of the liquid silicone 132 by the pre-formed polymer 130. Thus, stronger adhesion is promoted by the high degree of interdigitation which results from wetting of the surface of the pre-formed polymer 130 with the liquid silicone 132.

Figure 3A:
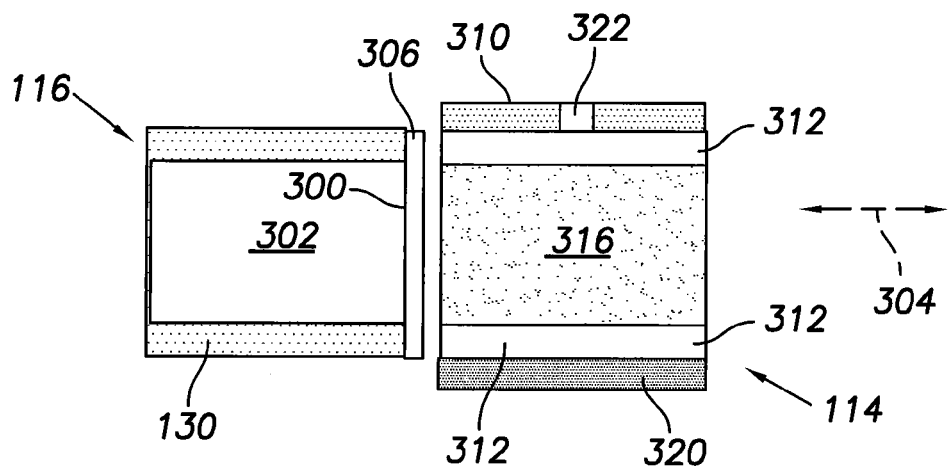
FIGS. 3A-C are schematic illustrations of one embodiment of a molding process for forming a molded section which joins the proximal and distal portions of the lead body; (A) preparation of the proximal portion of the lead body for insertion within a mold; (B) infiltration of the mold with a liquid polymer to be molded; (C) the composite lead body following curing of the molded polymer.

In reference to FIGS. 2 and 3A, in a first step 202 of the method 200, the pre-formed polymer 130 is provided. In one embodiment, the polymer 130 is pre-formed in a generally tubular shape, containing a cavity 302 for use in containment of the electrical conductor (not shown). In one embodiment, at least one end 300 of the polymer 130 adjacent to the distal portion 114 is oriented approximately normal to a longitudinal axis 304. In alternative embodiments, discussed in detail below in FIG. 4, the end 300 may adopt other configurations in order to enhance the bonding between the polymers 130, 132 at the junctions 134.

In a second step 204 of the method 200, the end 300 of the proximal portion 130 is treated with a primer 306 so as to facilitate bonding with the molded silicone polymer 132. As discussed above, traditional adhesives fail to provide adequate strength or geometric tolerances when joining materials such as silicone and silicone-polyurethane co-polymers. The primer 306 promotes adhesion between the surfaces of the two polymers 130, 132, which would otherwise be substantially incapable of forming a strong bond due to poor wetting. In general, the primer 306 possesses at least two reactive groups, a first group compatible with a first surface and a second group compatible with a second surface. For example, the first and second surfaces may comprise silicone-polyurethane co-polymers and silicone polymers 130, 132. The primer 306 is applied to the polymers 130 about the surfaces intended to bond with the molded silicone 132, such as the end 300. The primer 306 forms a film which reacts with the polymer surfaces and yields primed surfaces capable of substantially wetting the molded silicone polymer 132.

The primer 306 is applied to the end 300 of the pre-formed polymer 130 in accordance with the manufacturer's instructions. In one embodiment, the end 300 is cleaned and degreased with an appropriate solvent using a lint-free cloth, followed by rinsing with clean solvent. When the end 300 is dry, a coating of the primer 306 is applied. Application may comprise at least one of brushing, wiping, dipping, or any combination using a substantially lint-free cloth or brush, preferably a camel hair brush.

In one embodiment, the primer 306 may comprise a silicone primer 306. In general, the silicone primer 306 comprises at least one or more reactive silanes (e.g. alkoxy silanes), a condensation catalyst, and a solvent carrier (e.g. water). In a preferred embodiment, the silicone primer may comprise one of SP-135 and SP-142 silicone primers, commercially produced by NuSil Technology (Carpinteria, Calif.). SP-135 is a formulation of naphtha, tetra-n-propyl silicate, tetragutyltitanate, and tetra (2-methodxyethoxy) silane, while SP-142 is a formulation of naphtha, methacryloxypropyltrimethoxysilane, and tetrabutyltitanate. In one embodiment, the primer 306 is allowed to dry for approximately 30 minutes, at about room temperature (22° C.) and a relative humidity of about 50%.

In a third step 206 of the method, 200, the pre-formed polymer 130 is introduced into a mold 310. In one embodiment, the mold 310 comprises a positive mold 310 having inner and outer sections 316, 320 configured to mate with the end 300 of the pre-formed polymer 130. The mold is formed from a material which is chemically compatible with the molded silicone polymer 132, such as highly polished chrome-plated or stainless steel materials. The inner section 316 of the mold 310 comprises a solid, generally cylindrical body which is placed within the cavity 302 of the pre-formed polymer 130. The outer portion 320 of the mold 310 comprises a generally cylindrical tube which is configured for placement about the outer surfaces of the pre-formed polymer 130. In one embodiment, the outer section 320 may comprise a semi-mold. So positioned, the mold 310 and the pre-formed polymer 130 form a mold cavity 312 into which the molded silicone polymer 132 is introduced, for example, through an opening 322 in the outer section 320 of the mold 310, as discussed below. A mold release agent may also be applied to the surfaces of the mold 310 which are in contact with the polymers 130, 132 in order to facilitate de-molding.

Figure 3B:
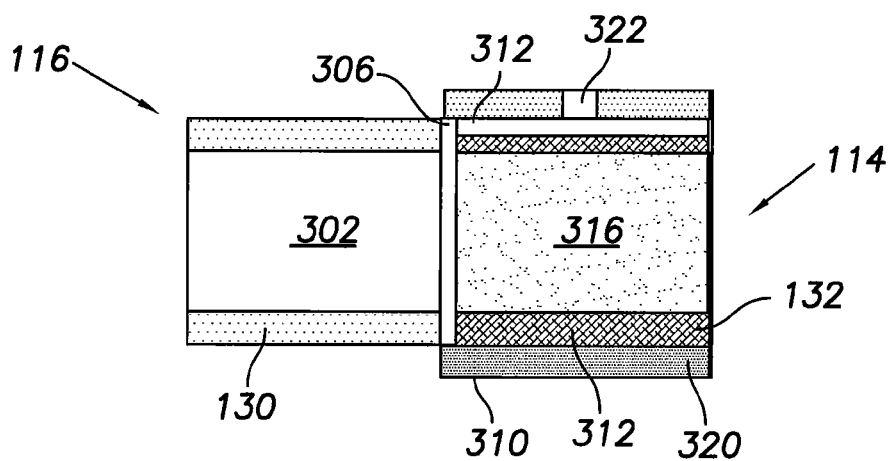

In a fourth step 210, the molded silicone polymer 132 is introduced into the mold 310 in an uncured, liquid state, as illustrated in FIG. 3B. The silicone polymer 132 may comprise, in one embodiment, a medical grade, silicone polymer 132 as known in the art. For example, the molded silicone polymer 132 may comprise one of addition cure and platinum cure silicone polymers. The molded silicone polymer 132 is prepared for molding according to the manufacturer's instructions. Subsequently, the molded silicone polymer 132 is poured into the mold 310 so as to substantially fill the mold cavity 312. Vacuum pressure may optionally be applied to the mold 310 so as to substantially extract any air which may be present within the mold cavity 312, avoiding the formation of strength reducing flaws (e.g. voids) within the molded silicone 132. The vacuum pressure further displaces air within the peaks and valleys of the surfaces of the pre-formed polymer 130 adjacent the mold cavity 312, facilitating interdigitation of the molded polymer 132 with the pre-formed polymer 130.

In fifth step and sixth steps 212, 214 of the method 200, the molded silicone polymer 132 is cured and demolded. In one embodiment, the mold 310 is heated to an elevated temperature within the range of approximately 100-200° C. for between approximately 2-10 minutes. Following this cure treatment, the mold 310 is subjected to a post-cure treatment comprising further heating of the mold 310 to a temperature of between approximately 100-200° C. for between approximately 1-3 hours. The molded silicone polymer 132 is then stabilized by a rest period of between approximately 1-3 hours at approximately ambient temperature and humidity.

Figure 4A:
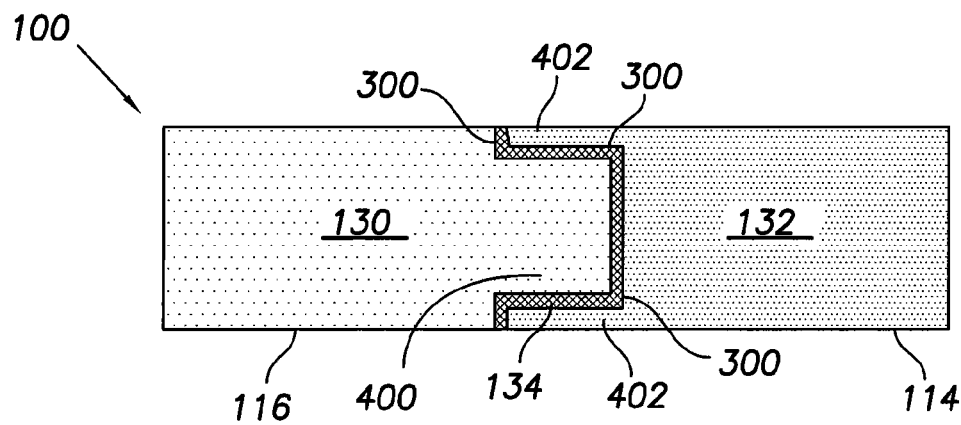
FIGS. 4A-C are schematic illustrations of embodiments of end geometries of the pre-formed proximal portion of the lead body which increase the length of the junction between the proximal portion of the lead body and the molded section; (A) lap joints; (B) peaks and valleys; (C) a combination of (A) and (B)
Figure 4B:
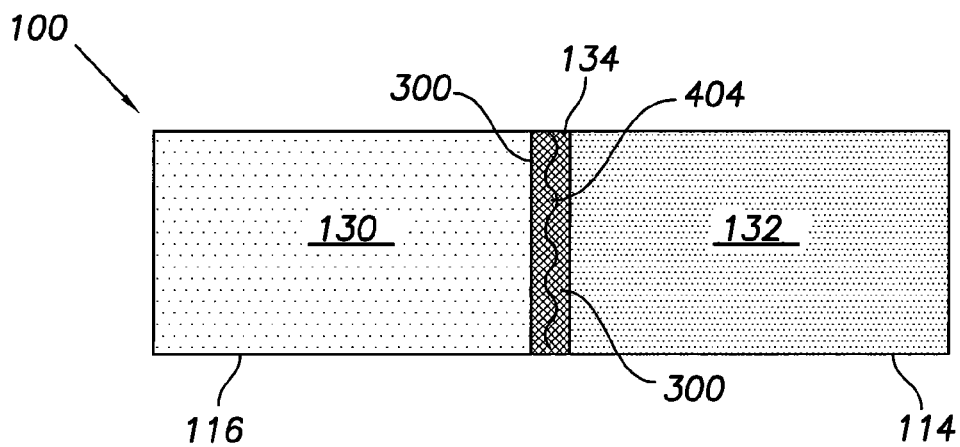
Figure 4C:
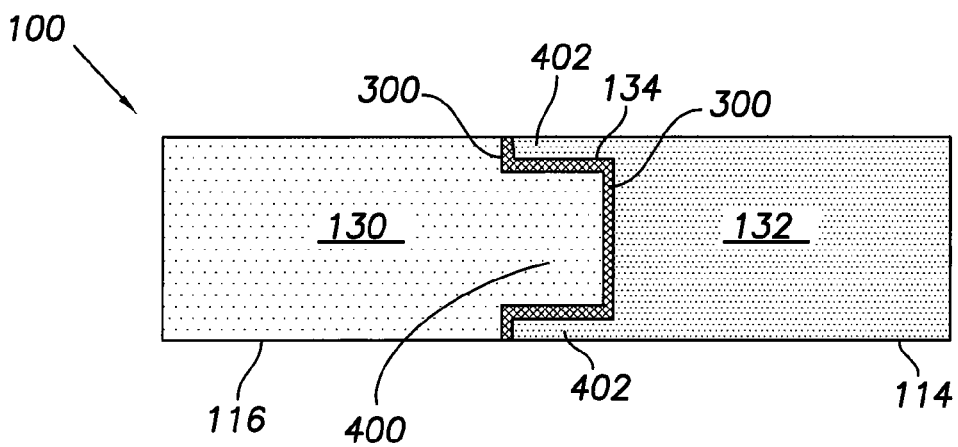

In alternative embodiments of the present invention, the ends 300 of the pre-formed polymer 130 may be configured to enhance the bonding obtained at the junction 134 with the molded silicone polymer 132. In one embodiment, this may be accomplished by providing a pre-formed polymer 130 having one or more ends 300 which lengthen the junction 134 when the molded silicone portion 132 is formed. FIGS. 4A-4C illustrate several non-limiting embodiments of the ends 300.

For example, as illustrated in FIG. 4A, a portion 400 of the end 300 of the pre-formed co-polymer 130 may be cut away to form a C-shape. When the molded polymer 132 is formed, it enters the portion 400. In this manner, the molded silicone polymer 132 forms lap joints 402 with the pre-formed polymer 130, where the molded silicone polymer 132 substantially overlaps with the pre-formed polymer 130 along the axis of the lead 100. Alternatively, as illustrated in FIG. 4B, a plurality of peaks and valleys 404 may be introduced into the end 300 of the pre-formed co-polymer 130. The molded polymer 132 substantially follows the peaks and valleys 404, lengthening the junction 134 between the polymers 130, 132 over that which would be obtained from a substantially straight junction 134. The amplitude and period of the peaks and valleys 404 may also be adjusted to change the length of the junction 134. In further embodiments, illustrated in FIG. 4C, the ends 300 of the pre-formed polymer 130 may be configured to provide combinations both lap joints 402 and peaks and valleys 404.

The molding techniques discussed above provide several advantages over traditional polymer lead fabrication. Conventional joining techniques, such as the use of medical adhesives, bond poorly to silicone materials, owing to the low surface energy of the silicones which inhibits wetting, reducing the area of the bond and subsequent adhesion. Adhesives further increase the diameter about the junction region, resulting in a bulge which can hinder the travel of heart stimulation leads through the veins. Further, when using adhesives to bond pre-formed polymer in the proximal and distal portions, the interior passage from one portion of the lead to the next is generally not co-axial. This may inhibit insertion of the electrical conductor through the junction. Alternatively, the junction may rub against the electrical conductor, causing the electrical conductor to wear, fray, or even become severed over time.

The embodiments of the composite leads 100 disclosed herein are less subjected to these problems. In one aspect, the molded silicone polymer 132 creates a strong bond with the silicone-polyurethane co-polymer 130. Priming the surfaces of the pre-formed polymer 130 allows the molded silicone polymer 132 to substantially wet the surface of the pre-formed polymer 130 and enter the peaks and valleys within the surface of the pre-formed polymer 130. Thus, interdigitation between the polymers 130, 132 is facilitated substantially throughout the junction 134. Further, forming the molded silicone polymer 132 by in-situ molding allows negative and positive pressures to be applied to the mold 310 during the molding process, substantially removing potential weakening defects from the molded silicone polymer 132 (e.g. air bubbles) and forcing the molded silicone polymer into the peaks and valleys within the surface of the pre-formed polymer 130, further promoting interdigitation.

Figure 3C:
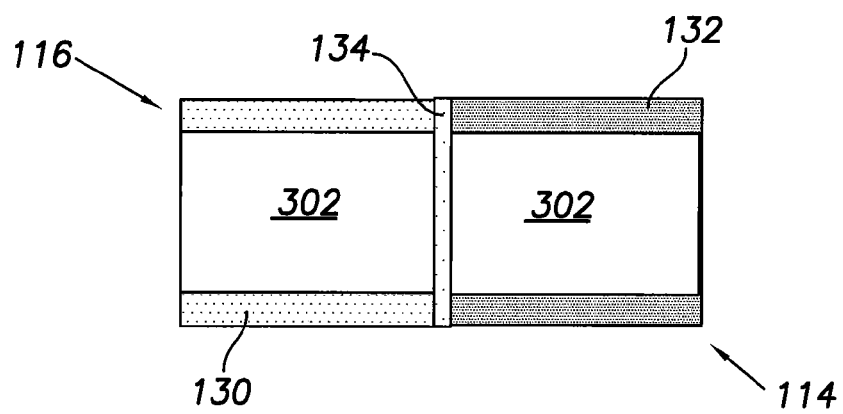

In another aspect, forming the composite leads 100 through the above described molding process provides significant control over the dimensions of the junction 134 formed between the polymers 130, 132. As illustrated in FIGS. 3A-C, the molded silicone polymer 132 is formed within the confines of the mold cavity 312. By providing a mold 310 having a mold cavity 312 whose outer surface is substantially continuous with the outer surface of the pre-formed polymers 130, the molded polymer 132 and the junctions 134 formed between the polymers 130, 132 possess substantially the same outer dimensions as the pre-formed polymer 130, providing lead body 120 having a substantially smooth, continuous surface which is substantially devoid of bulges about the molded polymer 132 and junctions 134.

In another aspect, the molding process substantially aligns the cavities 302 of the portion polymers 130, 132. When placing the pre-formed polymer 130 within the mold 310, the mold 310 secures the end 300 of the pre-formed polymers 130 with respect to the mold 310. As such, the inner section 316 of the mold 310 is substantially co-axial with the cavity of the pre-formed polymer 130. Because the inner section 316 of the mold 310 defines the cavity 302 of the molded silicone polymer 132, this orientation ensures that the cavities 302 of the polymers 130, 132 are substantially co-axial when the molded silicone polymer 132 is cured. Advantageously, the co-axial nature of the cavity 302 prevents discontinuities within the surface of the cavity 302 which might obstruct the electrical conductor 122 or rub against the electrical conductor 122 and cause wear damage in either the lead body 120 or electrical conductor 122.

Figure 5:
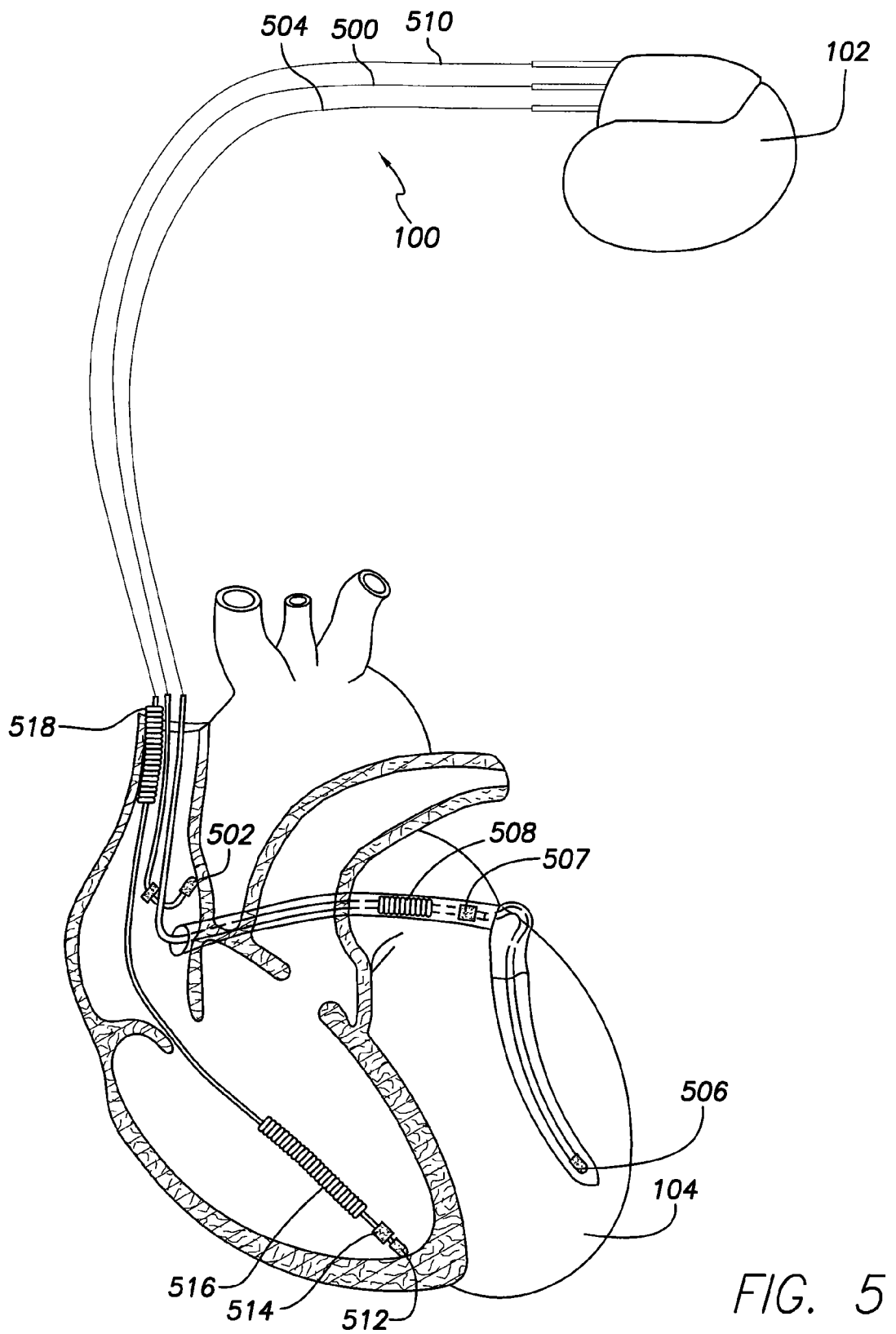
FIG. 5 is a schematic illustration of one embodiment of an implanted cardiac stimulation device, such as a pacemaker or ICD, in electrical communication with at least three composite heart stimulation leads of the present invention for delivering multi-chamber stimulation and shock therapy.

Embodiments of the composite heart stimulation leads, 100, may be utilized in stimulation devices which are configured for delivering multi-chamber stimulation and shock therapy. To sense atrial cardiac signals, and to provide right atrial chamber stimulation therapy, the stimulation device 102 is coupled to an implantable right atrial lead 500 having at least an atrial tip electrode 502, which typically is implanted in the patient's right atrial appendage. To sense left atrial and ventricular cardiac signals and to provide left chamber pacing therapy, the stimulation device 102 is coupled to a "coronary sinus" lead 504 designed for placement in the "coronary sinus region" via the coronary sinus ostium (OS) for positioning a distal electrode adjacent to the left ventricle and/or additional electrode(s) adjacent to the left atrium, as illustrated in FIG. 5. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 504 is designed to receive atrial and ventricular cardiac signals and to deliver left ventricular pacing therapy using at least a left ventricular tip electrode 506, left atrial pacing therapy using at least a left atrial ring electrode 507, and shocking therapy using at least a left atrial coil electrode 508.

The stimulation device 102 is also shown in electrical communication with the patient's heart 104 by way of an implantable right ventricular lead 510 having, in this embodiment, a right ventricular tip electrode 512, a right ventricular ring electrode 514, a right ventricular (RV) coil electrode 516, and a superior vena cava (SVC) coil electrode 518. Typically, the right ventricular lead 510 is transvenously inserted into the heart 104 so as to place the right ventricular tip electrode 512 in the right ventricular apex so that the RV coil electrode 516 will be positioned in the right ventricle and the SVC coil electrode 518 will be positioned in the superior vena cava. Accordingly, the right ventricular lead 510 is capable of receiving cardiac signals, and delivering stimulation in the form of pacing and shock therapy to the right ventricle.

Figure 6:
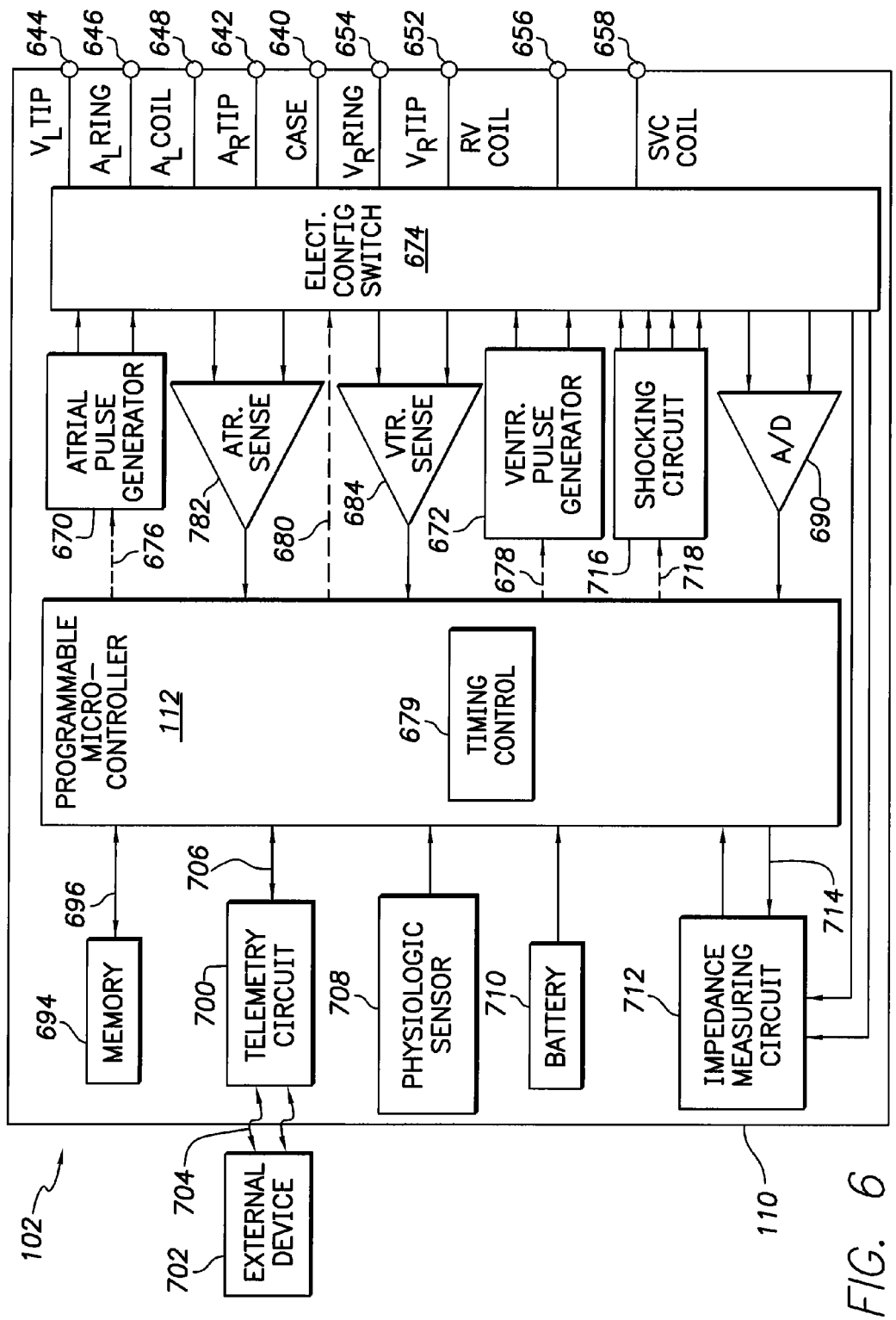
FIG. 6 is a functional block diagram of a multi-chamber implantable stimulation device for use with the composite heart stimulation leads of the present invention, illustrating the basic elements of a stimulation device which can provide cardioversion, defibrillation and pacing stimulation in four chambers of the heart.

As illustrated in FIG. 6 a simplified block diagram is shown of the multi-chamber implantable stimulation device 102, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

The housing 110 for the stimulation device 102, shown schematically in FIG. 5, is often referred to as the "can", "case" or "case electrode" and may be programmably selected to act as the return electrode for all "unipolar" modes. The housing 110 may further be used as a return electrode alone or in combination with one or more of the coil electrodes, 508, 516 and 518, for shocking purposes. The housing 110 further includes a connector (not shown) having a plurality of terminals, 642, 644, 646, 648, 652, 654, 656, and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 502.

To achieve left chamber sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular tip electrode 506, the left atrial ring electrode 507, and the left atrial coil electrode 508, respectively.

To support right chamber sensing, pacing and shocking, the connector further includes a right ventricular tip terminal ($V_R$ TIP) 652, a right ventricular ring terminal ($V_R$ RING) 654, a right ventricular shocking terminal (Rv COIL) 656, and an SVC shocking terminal (SVC COIL) 658, which are adapted for connection to the right ventricular tip electrode 512, right ventricular ring electrode 514, the RV coil electrode 516, and the SVC coil electrode 518, respectively.

At the core of the stimulation device 102 is a programmable microcontroller 112 which controls the various modes of stimulation therapy. As is well known in the art, the microcontroller 112 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 112 includes the ability to process or monitor input signals (data) as controlled by a program code stored in a designated block of memory. The details of the design and operation of the microcontroller 112 are not critical to the invention. Rather, any suitable microcontroller 112 may be used that carries out the functions described herein. The use of microprocessor-based control circuits for performing timing and data analysis functions are well known in the art.

As shown in FIG. 6, an atrial pulse generator 670 and a ventricular pulse generator 672 generate pacing stimulation pulses for delivery by the right atrial lead 500, the right ventricular lead 510, and/or the coronary sinus lead 504 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators, or shared pulse generators. The pulse generators, 670 and 672, are controlled by the microcontroller 112 via appropriate control signals, 676 and 678, respectively, to trigger or inhibit the stimulation pulses.

The microcontroller 112 further includes timing control circuitry 679 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 674 includes a plurality of switches for connecting the desired electrodes to the appropriate I/O circuits, thereby providing complete electrode programmability. Accordingly, the switch 674, in response to a control signal 680 from the microcontroller 112, determines the polarity of the stimulation pulses (e.g., unipolar, bipolar, combipolar, etc.) by selectively closing the appropriate combination of switches (not shown) as is known in the art. In this embodiment, the switch 674 also supports simultaneous high resolution impedance measurements, such as between the case or housing 110, the right atrial electrode 502, and right ventricular electrodes 512, 508 as described in greater detail below.

Atrial sensing circuits 682 and ventricular sensing circuits 684 may also be selectively coupled to the right atrial lead 500, coronary sinus lead 504, and the right ventricular lead 510, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers, or shared amplifiers. The switch 674 determines the "sensing polarity" of the cardiac signal by selectively closing the appropriate switches, as is also known in the art. In this way, the clinician may program the sensing polarity independently of the stimulation polarity.

Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables the device 102 to deal effectively with the difficult problem of sensing the low amplitude signal characteristics of atrial or ventricular fibrillation. The outputs of the atrial and ventricular sensing circuits, 582 and 684, are connected to the microcontroller 112 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, the device 102 utilizes the atrial and ventricular sensing circuits, 682 and 684, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 112 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (ND) data acquisition system 690. The data acquisition system 690 is configured to acquire intracardiac electrogram (IEGM) signals, convert the raw analog data into a digital signal, and store the digital signals for later processing and/or telemetric transmission to an external device 102. The data acquisition system 690 is coupled to the right atrial lead 500, the coronary sinus lead 504, and the right ventricular lead 510 through the switch 674 to sample cardiac signals across any pair of desired electrodes.

The microcontroller 112 is further coupled to a memory 694 by a suitable data/address bus 696, wherein the programmable operating parameters used by the microcontroller 112 are stored and modified, as required, in order to customize the operation of the stimulation device 102 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 104 within each respective tier of therapy.

Advantageously, the operating parameters of the implantable device 102 may be non-invasively programmed into the memory 694 through a telemetry circuit 700 in telemetric communication with the external device 702, such as a programmer, transtelephonic transceiver, or a diagnostic system analyzer. The telemetry circuit 700 is activated by the microcontroller by a control signal 706. The telemetry circuit 700 advantageously allows IEGMs and status information relating to the operation of the device 102 (as contained in the microcontroller 112 or memory 694) to be sent to the external device 702 through an established communication link 604.

In the preferred embodiment, the stimulation device 102 further includes a physiologic sensor 708, commonly referred to as a "rate-responsive" sensor because it is typically used to adjust pacing stimulation rate according to the exercise state of the patient. However, the physiological sensor 708 may further be used to detect changes in cardiac output, changes in the physiological condition of the heart, or diurnal changes in activity (e.g., detecting sleep and wake states). Accordingly, the microcontroller 112 responds by adjusting the various pacing parameters (such as rate, AV Delay, V-V Delay, etc.) at which the atrial and ventricular pulse generators, 670 and 672, generate stimulation pulses.

The stimulation device additionally includes a battery 710 which provides operating power to all of the circuits shown in FIG. 6. For the stimulation device 102, which employs shocking therapy, the battery 710 must be capable of operating at low current drains for long periods of time and then be capable of providing high-current pulses (for capacitor charging) when the patient requires a shock pulse. The battery 710 must also have a predictable discharge characteristic so that elective replacement time can be detected. Accordingly, embodiments of the device 102 including shocking capability preferably employ lithium/silver vanadium oxide batteries. For embodiments of the device 102 not including shocking capability, the battery 710 is preferably lithium iodide or carbon monoflouride or a hybrid of the two.

As further shown in FIG. 6, the device 102 is shown as having an impedance measuring circuit 712 which is enabled by the microcontroller 112 via a control signal 714.

In the case where the stimulation device 102 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 112 further controls a shocking circuit 716 by way of a control signal 718. The shocking circuit 716 generates shocking pulses of low (up to 0.5 joules), moderate (0.5-10 joules), or high energy (11 to 40 joules), as controlled by the microcontroller 112. Such shocking pulses are applied to the patient's heart 104 through at least two shocking electrodes, and as shown in this embodiment, selected from the left atrial coil electrode 508, the RV coil electrode 516, and/or the SVC coil electrode 518. As noted above, the housing 110 may act as an active electrode in combination with the RV electrode 516, or as part of a split electrical vector using the SVC coil electrode 518 or the left atrial coil electrode 508 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 112 is capable of controlling the synchronous or asynchronous delivery of the shocking pulses.

Many patients have conditions which indicate that they be provided with a therapeutic cardiac therapy device. Embodiments of the invention are based at least in part on utilizing an implantable cardiac stimulation device, such as the device 102 previously described, for ongoing monitoring of the patient's condition. Certain embodiments utilize analysis based on sensing which is performed by the device 102 and can be utilized for other purposes, such as determining need for therapy delivery as previously described. Various embodiments are adapted for early detection of an emerging condition and to keep a record of data related to the emerging condition. These embodiments facilitate early detection of an emerging condition which may not manifest itself during a scheduled clinical evaluation. Certain embodiments also provide the ability to track or generate trend data, for example for monitoring for changes in a known or preexisting condition where the changes may indicate revision of a patient's therapy or other intervention.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. A method of forming a lead body using a) a pre-formed tube comprising a first polymer, the pre-formed tube having a longitudinal axis, a cavity along the longitudinal axis configured for containment of an electrical conductor, and an annular end oriented generally normal to the longitudinal axis, and b) a mold having an inner cylindrical section and an outer tubular section surrounding the inner section and separated there from to form a space defining a tubular positive mold, said method comprising:
    applying a primer to the end of the pre-formed tube;
    positioning the end of the pre-formed tube into the space of the mold to thereby align the cavity of the pre-formed tube with the inner cylindrical section of the mold, and to thereby close an end of the tubular positive mold to form a mold cavity;
    introducing a liquid second polymer into the mold cavity near the end of the pre-formed tube; and
    curing the liquid second polymer to form a molded tube having a longitudinal axis and an annular end oriented generally normal to the longitudinal axis, wherein the end of the molded tube is joined to the end of the pre-formed tube at a junction.

2. The method of claim 1 wherein the second polymer substantially wets the primed end of the pre-formed tube.

3. The method of claim 1 further comprising contouring the end of the pre-formed tube adjacent to the junction prior to introducing the liquid second polymer into the mold.

4. The method of claim 3 wherein contouring the end of the pre-formed tube comprises cutting away a portion of the pre-formed tube.

5. The method of claim 3 wherein contouring the end of the pre-formed tube comprises forming ridges and valleys in the end of the pre-formed tube.

6. The method of claim 1 wherein the pre-formed tube comprises an outer surface and positioning comprises placing the outer tubular section of the mold about the outer surface of the pre-formed tube.

7. The method of claim 6 wherein the inner diameter of the outer tubular section of the mold and the outer diameter of the pre-formed tube are such that the inner surface of the outer tubular section is in abutting contact with the outer surface of the pre-formed tube when the mold is positioned about the outer surface of the pre-formed tube.

8. The method of claim 1 wherein positioning comprises placing the inner section of the mold in the cavity of the pre-formed tube.

9. The method of claim 8 wherein the diameter of the inner section and the diameter of the cavity are such that the outer surface of the inner section is in abutting contact with the inner wall of the pre-formed tube when positioned in the cavity.

10. The method of claim 1 wherein introducing comprises applying positive pressure to the mold to substantially fill the mold cavity with liquid second polymer.

11. The method of claim 1 wherein introducing comprises applying vacuum pressure to the mold after the mold cavity has been substantially filled with liquid second polymer.

12. The method of claim 1 wherein the first polymer comprises a co-polymer.

13. The method of claim 12 wherein the co-polymer comprises a silicone-polyurethane co-polymer.

14. The method of claim 1 wherein the second polymer comprises a silicone.

15. The method of claim 1 wherein the primer comprises a silicone primer.

16. A lead body formed by:
    obtaining a) a pre-formed tube comprising a first polymer, the pre-formed tube having a longitudinal axis, a cavity along the longitudinal axis configured for containment of an electrical conductor, and an annular end oriented generally normal to the longitudinal axis, and b) a mold having an inner cylindrical section and an outer tubular section surrounding the inner section and separated there from to form a space defining a tubular positive mold;
    applying a primer to the end of the pre-formed tube;
    positioning the end of the pre-formed tube into the space of the mold to thereby align the cavity of the pre-formed tube with the inner cylindrical section of the mold, and to thereby close an end of the tubular positive mold to form a mold cavity;
    introducing a liquid second polymer into the mold cavity near the end of the pre-formed tube; and
    curing the liquid second polymer to form a molded tube having a longitudinal axis and an annular end oriented generally normal to the longitudinal axis, wherein the end of the molded tube is joined to the end of the pre-formed tube at a junction.

17. The lead body of claim 16 further formed by contouring the end of the pre-formed tube adjacent to the junction prior to introducing the liquid second polymer into the mold.

18. The lead body of claim 17 wherein contouring the end of the pre-formed tube comprises cutting away a portion of the pre-formed tube.

19. The lead body of claim 17 wherein contouring the end of the pre-formed tube comprises forming ridges and valleys in the end of the pre-formed tube.

20. A stimulation lead for use with an implantable cardiac stimulation device, said lead comprising:
    a lead body formed by:
        obtaining a) a pre-formed tube comprising a first polymer, the pre-formed tube having a longitudinal axis, a cavity along the longitudinal axis configured for containment of an electrical conductor, and an annular end oriented generally normal to the longitudinal axis, and b) a mold having an inner cylindrical section and an outer tubular section surrounding the inner section and separated there from to form a space defining a tubular positive mold;
        applying a primer to the end of the pre-formed tube;
        positioning the end of the pre-formed tube into the space of the mold to thereby align the cavity of the pre-formed tube with the inner cylindrical section of the mold, and to thereby close an end of the tubular positive mold to form a mold cavity;
        introducing a liquid second polymer into the mold cavity near end of the pre-formed tube; and curing the liquid second polymer to form a molded tube having a longitudinal axis and an annular end oriented generally normal to the longitudinal axis, wherein the end of the molded tube is joined to the end of the pre-formed tube at a junction;

at least one electrode carried by the lead body; and a conductor wire within the lead body and electrically coupled to the electrode.

\* \* \* \* \*